United States Patent
Chopra

(10) Patent No.: US 7,010,086 B2
(45) Date of Patent: Mar. 7, 2006

(54) THREE-DIMENSIONAL X-RAY IMAGING SYSTEM

(75) Inventor: Nasreen Chopra, Belmont, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 64 days.

(21) Appl. No.: 10/758,934

(22) Filed: Jan. 15, 2004

(65) Prior Publication Data

US 2005/0157841 A1 Jul. 21, 2005

(51) Int. Cl.
*G21K 1/12* (2006.01)
*H01G 1/64* (2006.01)

(52) U.S. Cl. .................... 378/22; 378/98.8; 378/19; 250/370.09

(58) Field of Classification Search ............ 378/4, 378/8, 19, 21, 22, 23, 24, 26, 25, 98.8, 901, 378/41, 62; 250/370.09, 370.11
See application file for complete search history.

(56) References Cited

U.S. PATENT DOCUMENTS

| | | | | |
|---|---|---|---|---|
| 4,349,740 A | * | 9/1982 | Grassmann et al. | 378/25 |
| 5,461,653 A | * | 10/1995 | Parker | 378/22 |
| 5,592,523 A | * | 1/1997 | Tuy et al. | 378/19 |
| 6,424,375 B1 | * | 7/2002 | Fowler | 348/241 |
| 6,628,745 B1 | * | 9/2003 | Annis et al. | 378/21 |
| 6,674,837 B1 | * | 1/2004 | Taskar et al. | 378/122 |

* cited by examiner

*Primary Examiner*—Edward J. Glick
*Assistant Examiner*—Irakli Kiknadze

(57) ABSTRACT

An imaging system for generating an image of a planar segment of an object is disclosed. The imaging system includes an x-ray source, a planar detector, and a controller. The x-ray source generates x-rays from first and second source points, the x-rays from the first and second source points passing through the object. The planar detector includes a plurality of photodetectors covered by a layer of scintillation material that converts x-rays into visible light, the planar detector is positioned to receive x-rays from the first and second source points after the x-rays have passed through the object. The controller selects which of the source points generates the x-rays at any given time. The controller reads a first image formed by x-rays from the first source point and stored in a first portion of the planar detector while a second portion of the photodetectors measures x-rays from the second source point.

5 Claims, 6 Drawing Sheets

THREE-DIMENSIONAL X-RAY IMAGING SYSTEM

FIELD OF THE INVENTION

The present invention relates to three-dimensional x-ray imaging systems.

BACKGROUND OF THE INVENTION

In x-ray transmission imaging, illumination is projected through an object and the imaging signal results from a subtractive process, i.e. what is imaged is the far field of the illumination minus any signal that was absorbed, reflected or scattered. In many industries x-ray inspection is being used routinely for inspection of products in the manufacturing environments. Many of these applications require that a particular material be examined in the inspection process in spite of the presence of other materials that also absorb x-rays. For example, surface mounted integrated circuits are examined during manufacture to determine the distribution of solder on the assembly, which in turn, is related to the reliability of the assembly. In such systems, Cu traces, Si chips, and Fe in transformers all conspire to obscure, or 'shadow' the solder joints.

This shortcoming of projection imaging is overcome by CT (computed tomography) scanners. CT scanners combine information from a variety of projection viewpoints to overcome the shadowing and generate a 3D (three-dimensional) description of the object. A typical CT system measures the x-ray flux reaching a detector from a source that moves around the object. The object being scanned is modeled by a plurality of voxels having unknown x-ray absorbency. At each point, the measured flux represents the weighted sum of the x-ray absorbencies of each voxel along the path from the x-ray source to the detector. Different paths provide weighted sums involving different sets of voxels. If sufficient points are measured, a data processing system can solve the resulting system of equations for the x-ray absorbency of each voxel. The resulting data can then be analyzed or displayed as a three-dimensional model of the object that can be viewed from different viewpoints.

CT scanners are widely used for imaging the human body as part of diagnostic procedures. In principle and in limited practice, such scanners would be useful in imaging inanimate objects on assembly lines. Unfortunately, the cost of this equipment and its relatively low throughput has inhibited the use of CT scanners for such high volume applications.

One specialized form of tomographic scanning, known as laminography, is utilized in the inspection of printed circuit boards and other thin objects in which the image of a particular horizontal "slice" of the object is needed. In the case of a printed circuit board in which the solder layer is being inspected, only the slice on which the solder layer is placed is of interest. In laminography systems, a number of projection images of the object being examined are averaged together to form an image of one plane through the object. The images are chosen such that the plane of interest will generate the same image in each of the views while the planes above and below the plane of interest produce images that vary from image to image. When the images are summed, the images from the planes that are out of focus generate a diffuse background while the images from the in focus plane add constructively. To provide the averaging of the images, two of the three components of the system, the object, the x-ray source, and the detector, must move relative to the third. The earliest systems utilized a mechanical system in which an x-ray source and an imaging detector are rotated about an axis that is perpendicular to the focus plane. The imaging detector is generally a bulk scintillator with an optical system that images the image generated by the scintillator onto a CCD camera. The efficiency of this type of imaging system is a few percent. As a result, this type of system has a poor signal-to-noise ratio. To overcome this poor signal-to-noise ratio, the number of images that must be averaged must be increased, thereby decreasing the throughput of the inspection system. In addition, the cost associated with the mechanical system significantly increases the cost of the system.

Systems in which the motion of the two components is executed electrically are also known. For example, U.S. Pat. No. 6,324,249 describes a system in which a scanning x-ray source is combined with a very large x-ray detector consisting of a scintillator and a CCD imaging array. The x-ray source generates a point x-ray source that moves relative to the object. The scintillation detector is placed under the object and connected to the CCD array either by light pipes or a lens system that images the light output of the scintillator onto the CCD array. The CCD is configured as a two-dimensional array of detectors in which each column of detectors is readout by shifting the measured values from one-detector to the next in the column until the values leave one end of the column.

While such systems avoid the cost and time constraints imposed by systems that utilize mechanical motion, these systems are still too slow for many industrial applications. The scintillation detector is far from the CCD detector in embodiments that utilize a lens to form an image on the CCD array. As a result, the efficiency of the detector is relatively small, which leads to long integration times. Second, the CCD arrays are arranged such that the entire array must be readout for each x-ray image position, even though a small fraction of the array is needed for each x-ray position. As the array size is increased to accommodate larger printed circuit boards, the readout time becomes a significant fraction of the measurement time.

SUMMARY OF THE INVENTION

The present invention includes an imaging system for generating an image of a planar segment of an object. The imaging system includes an x-ray source, a planar detector, and a controller. The x-ray source generates x-rays from first and second source points, the x-rays from the first and second source points passing through the object. The planar detector includes a plurality of photodetectors covered by a layer of scintillation material that converts x-rays into visible light, the planar detector is positioned to receive x-rays from the first and second source points after the x-rays have passed through the object. The controller selects which source point generates the x-rays at any given time. The controller also reads a first image formed by x-rays from the first source point and stored in a first portion of the planar detector while a second portion of the photodetectors measures x-rays from the second source point to generate a second image that is stored in the second portion of the photodetectors. The controller combines the first and second images to form an image of a portion of the object. In one embodiment, the x-ray source includes a collimator for preventing x-rays generated from the second source point from reaching the first portion of the planar detector.

DETAILED DESCRIPTION OF PREFERRED EMBODIMENTS OF THE INVENTION

Figure 1:
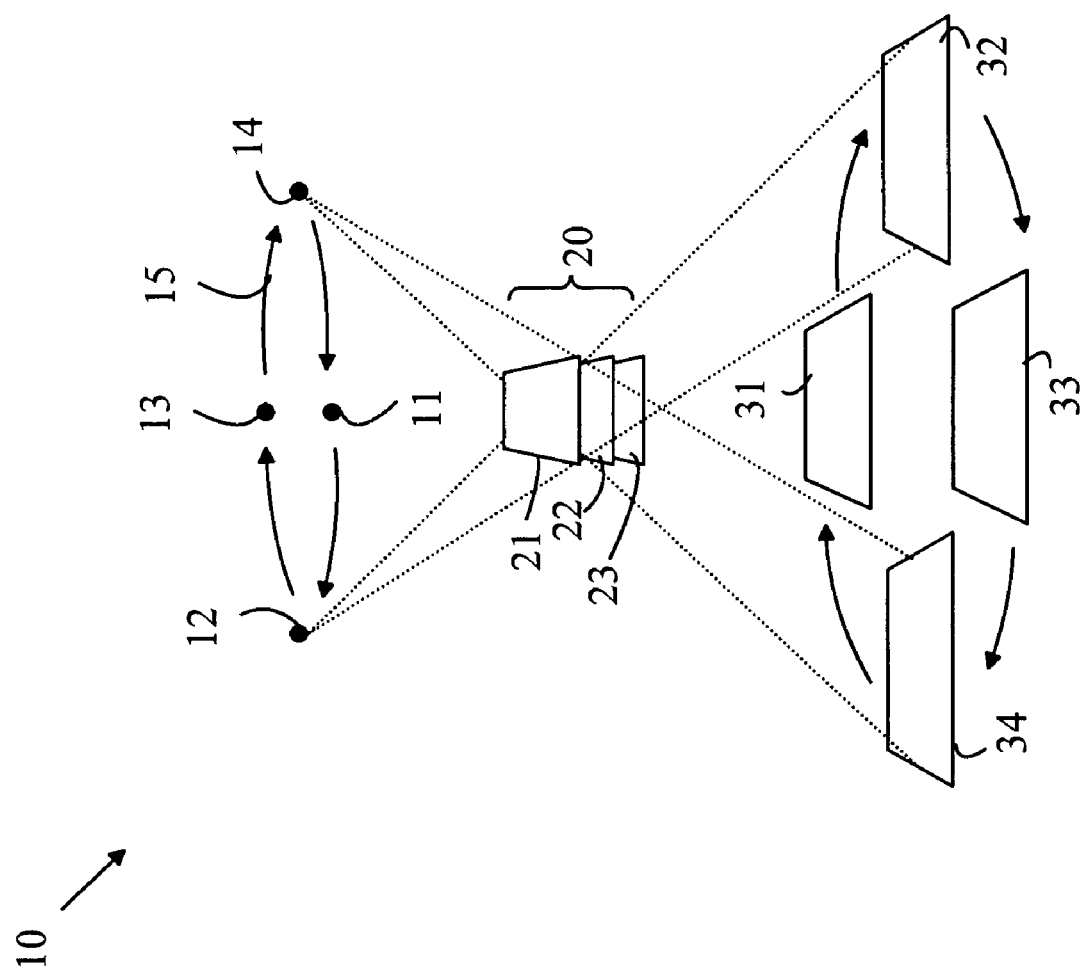
FIG. 1 illustrates a typical prior art laminography system.

The manner in which the present invention provides its advantages can be more easily understood with reference to FIG. 1, which illustrates a typical prior art laminography system 10 operating on an object 20. Three planes through object 20 are shown at 21–23. Plane 22 is the in-focus plane. Laminography system 10 includes an x-ray source and a detector. The x-ray source moves in a plane parallel to plane 22 around a path 15. Exemplary points on the path are shown at 11–14. The detector likewise moves in a plane that is parallel to plane 22. The detector locations corresponding to x-ray source positions 11–14 are shown at 31–34, respectively.

At each x-ray source and detector location, the x-ray source emits a cone of x-rays that casts a shadow on the region of interest in plane 22 onto the detector. This cone also casts a shadow of a portion of the object in plane 21 and a portion of the object in plane 23 onto the detector. Hence, the image at the detector is the sum of the images generated by plane 22 and portions of the object in planes 21 and 23. The x-ray source and detector are arranged such that the image obtained at each detector position is the sum of the image in the region of interest in plane 22 and portions of the object in planes 21 and 23. However, the portions of the object in planes 21 and 23 are different for different x-ray source positions. Hence, the sum of the images, when correctly rotated, consists of 4 copies of the image generated from plane 22 that add constructively, and various portions of the object in the other planes. Since the portions of the object in planes 21 and 23 differ from image location to image location, these images form an incoherent background, provided enough image locations are utilized.

The x-ray detector shown in FIG. 1 can be constructed from a moving detector that is rotated with the x-ray detector or a large detector that covers the area defined by all of the individual images. As noted above, systems that utilize a moving detector are expensive and relatively slow due to the limitations of the mechanical actuators. Systems that utilize a single large detector do not suffer from the mechanical limitations; however, these systems have poor efficiencies and require long readout times.

Figure 2A:
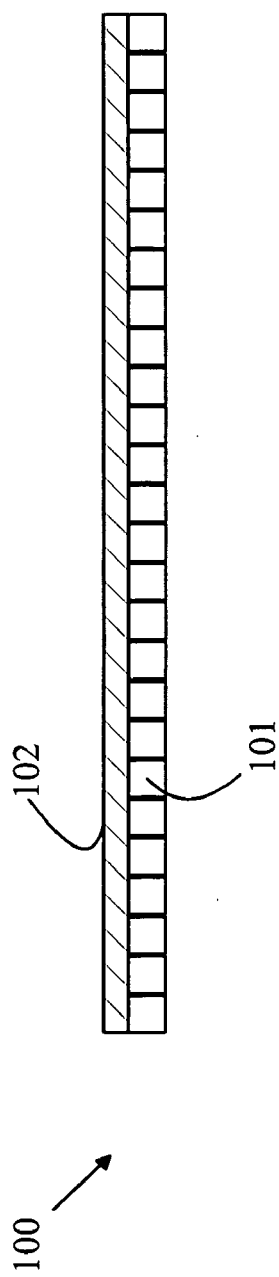
FIG. 2A is a cross-sectional view of one preferred embodiment of an x-ray detector for use in the present invention.
Figure 2B:
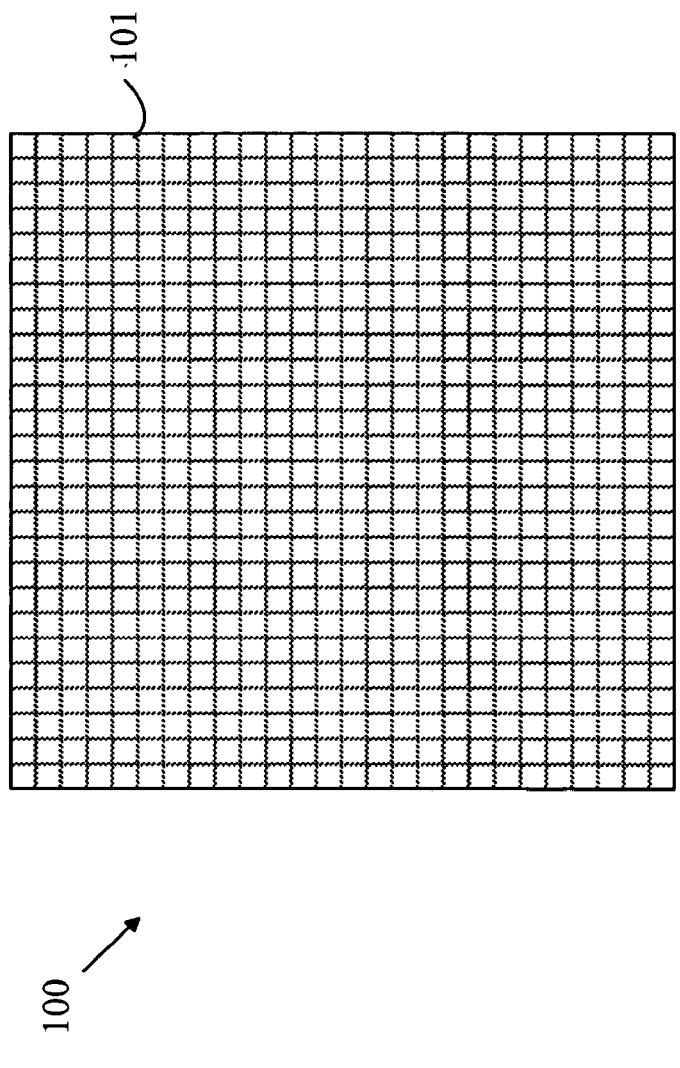
FIG. 2B is a top view of the x-ray detector shown in FIG. 2A.

Refer now to FIGS. 2A–B. FIG. 2A is a cross-sectional view of the preferred embodiment of an x-ray detector for use in the present invention. FIG. 2B is a top view of x-ray detector 100. X-ray detector 100 includes a plurality of photodetectors 101 that are organized into an array having a plurality of rows and columns. A layer 102 of scintillation material is deposited in close proximity to the photodetectors. The scintillation material converts an x-ray incident thereon into a visible light signal having a wavelength in a band that can be detected by the photodetectors. Since the layer 102 is located in close proximity to the photodetectors, the fraction of the light generated by the x-ray that reaches the photodetectors is substantially larger compared to prior art devices that utilize lens systems to image the output of the scintillation material onto the photodetectors. Detector arrays of the type shown in FIG. 2A–B are known in the x-ray arts where they are used in place of film in diagnostic radiology. Hence, these devices will not be discussed in detail here. Commercial detectors are available from a number of sources including Varian Associates and Trixell.

Figure 3:
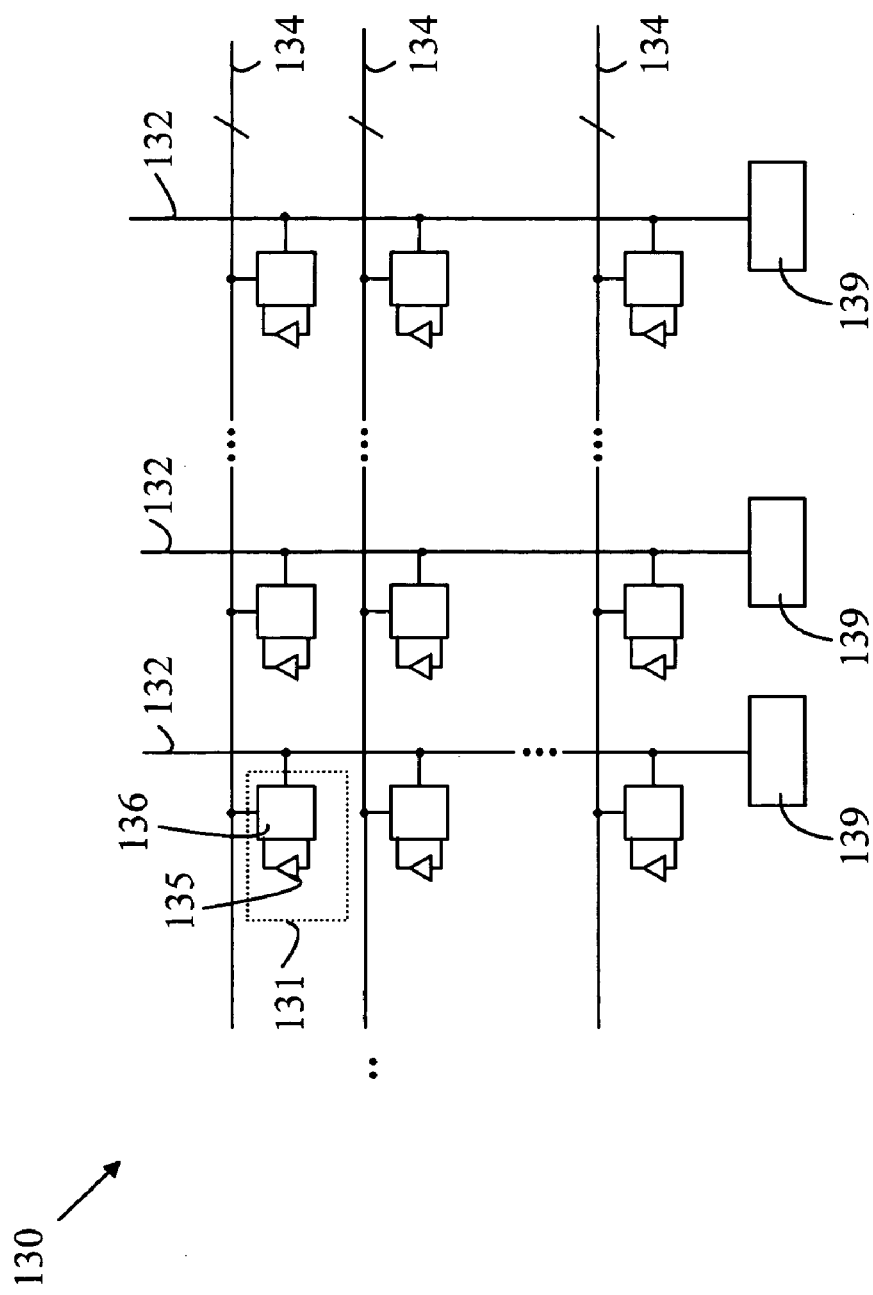
FIG. 3 is a simplified drawing of an array of photodiodes organized as a randomly accessible array of CMOS photodetectors.

In the preferred embodiment of the invention, the array of photodiodes is organized as a randomly accessible array of CMOS photodetectors. Arrays of CMOS photodetectors that are organized in a plurality of rows and columns in which any row can be read out separately and in any order are known to the art. A simplified drawing of such an array is shown in FIG. 3. Photodiode array 130 is constructed from a plurality of pixels 131 organized into rows and columns. Each pixel includes a photodiode 135 and an interface circuit 136. Each pixel generates a signal that is related to the total light received by the photodiode since the pixel was reset. This signal can be read without destroying the signal. Each pixel in a column is connected to a column readout line 132 by a gate circuit that is part of interface circuit 136. The pixel is connected to the readout line in response to a signal on the word line bus 134 to which the pixel is also connected. All of the pixels on a given word line bus are connected to the corresponding column readout lines together. Hence, all the pixels connected to a given word line bus may be viewed as a "word" that is readout simultaneously. A column readout circuit 139 is connected to each of the column readout lines and may include analog-to-digital converters for generating a digital value corresponding to the signal value at the pixel currently connected to the column readout line.

The word line buses, column readout circuits, and the interface circuits may also include circuitry for resetting the pixels. Since the details of the reset operation are not important in the present discussion, these aspects of the photodiode array will not be discussed in detail here. The manner in which the pixels are reset is discussed in detail in U.S. Pat. No. 6,424,375, which is hereby incorporated by reference.

The detector array of the present invention is large enough to accommodate all of the images that are generated at the various x-ray source positions without altering the position of the detector or object being scanned during the measurements. This feature substantially reduces the global imaging time. As noted above, the preferred photodiode array used in the present invention can be read out randomly. In particular, specific sections of the array can be read out without requiring other sections to be likewise read out and reset. It should also be noted that only a small fraction of the photodiode array is used for any given position of the x-ray spot. Hence, only the section currently being used needs to be read out. This substantially reduces the readout time for the image taken at each x-ray position.

Furthermore, by properly dividing the detector array into blocks, the time needed to reset the pixels can effectively be eliminated. If the photodiode array is divided into blocks such that the block currently accumulating data is separate from the previous block that was read out, the previously used block can be reset while the current block is accumulating data and being read-out. To reduce noise in CMOS photodetectors, each photodiode is preferably reset such that a predetermined voltage is applied across the photodiode in each pixel. Any variation in this reset voltage appears as noise in the image formed after the reset operation is complete. In one preferred embodiment of the invention, the reset operation ramps the voltage to a particular value and then allows the voltage to settle. This process can require an amount of time that is similar to that needed to accumulate the data and read out the pixels. Hence, an arrangement that allows this reset operation to be performed in the background is preferred. In such an arrangement, one block is reset while another block is being read out.

Figure 4:
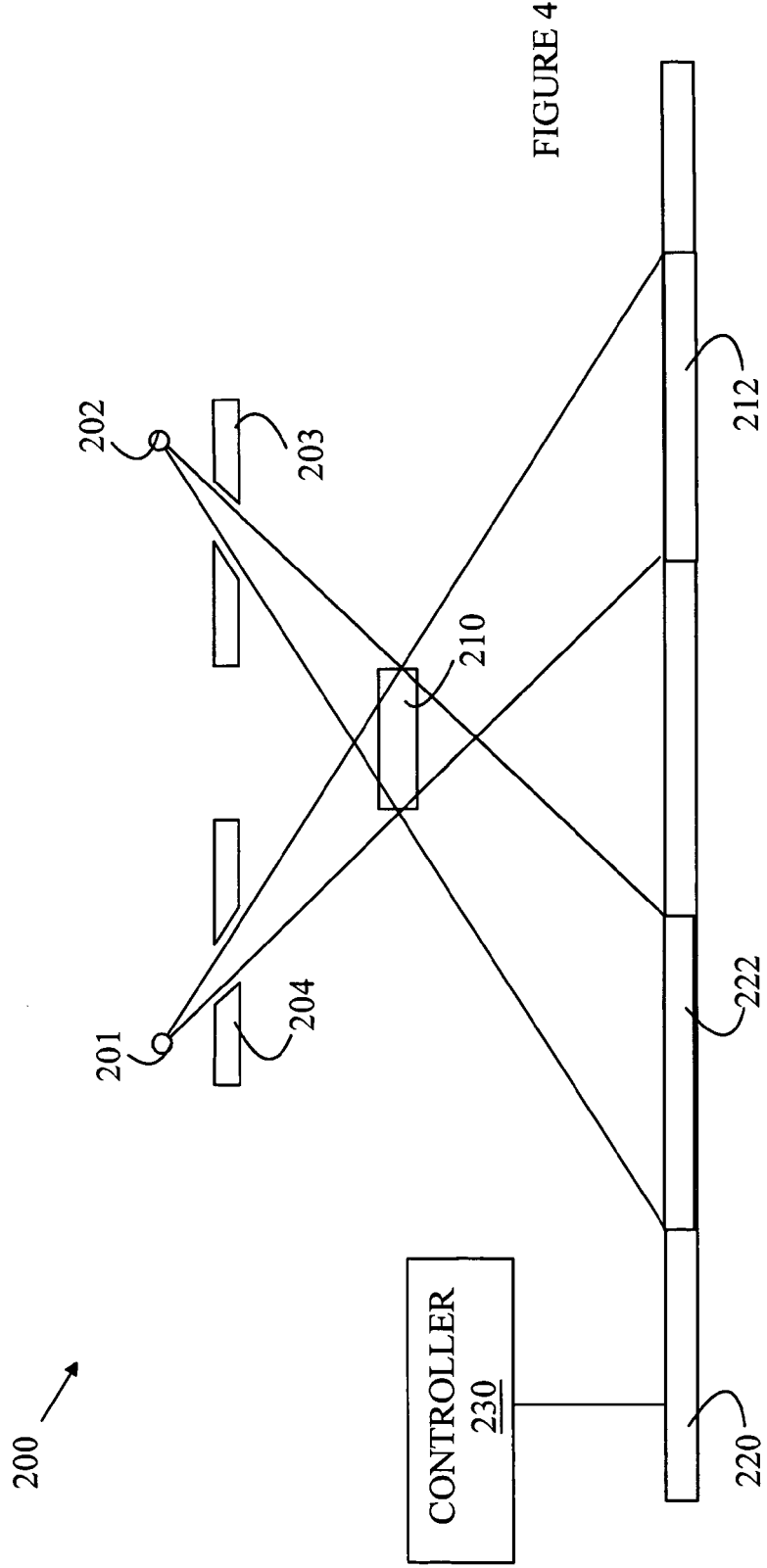
FIG. 4 is a cross-sectional view of an embodiment of the present invention in which the detection array is divided into blocks.

Refer now to FIG. 4, which is a cross-sectional view of an embodiment of the present invention in which the detection array is divided into blocks as described above. Laminography system 200 includes an x-ray source that generates x-rays at selected source positions. Exemplary source positions are shown at 201 and 202. The x-ray source is collimated by baffles shown at 203 and 204 such that the x-ray cone generated at each position passes through an object 210 that is being scanned and impinges on a defined area of detection array 220. The area of detector array 220 illuminated at source position 201 is shown at 212, and the area of detector array 220 illuminated at source position 202 is shown at 222. When the source position is switched from position 201 to 202, the photodetectors in region 212 are readout by controller 230 and are then reset while the photodetectors in region 222 are accumulating data. Controller 230 also combines the individual images to form the image of object 210 on the focal plane of laminography system 200.

In addition, controller 230 controls the x-ray source location that is currently operating. To simplify the drawings, the connections between the x-ray source and controller 230 have been omitted.

Figure 5:
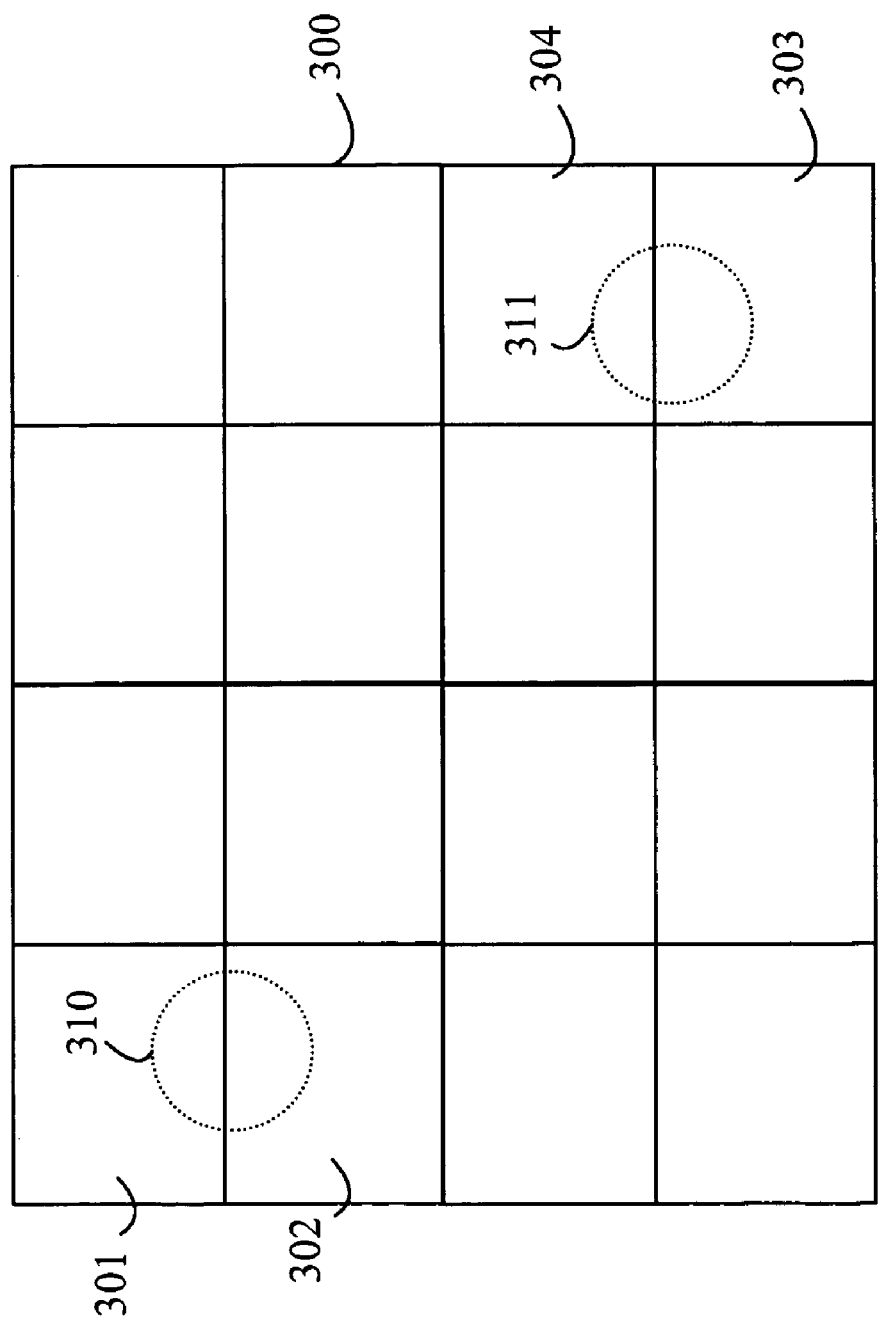
FIG. 5 illustrates one manner in which the x-ray detector can be divided into sub-arrays that provide an overlap feature.

Refer now to FIG. 5, which illustrates one manner in which the x-ray detector can be divided into sub-arrays that provide the above-described overlap feature. Array 300 is constructed from a plurality of sub-arrays. Exemplary sub-arrays are shown at 301–304. Each sub-array is organized as a plurality of rows and columns in a manner analogous to that discussed above. The photodetectors in each of the rows in a given sub-array are readout in parallel independently of the rows in the other sub-arrays. Hence, one or more of the sub-arrays can be accumulating data while others are being readout and reset.

The x-ray cones generated by the x-ray source at two locations are shown at 310 and 311. Cone 310 illuminates sub-arrays 301 and 302. Cone 311 illuminates sub-arrays 303 and 304. The order of the images taken by a laminography system utilizing array 300 is arbitrary. Hence, the order can be set such that successive images are diametrically opposed relative to the center of array 300, and the readout and reset operations for one image can thus be overlapped with the data accumulation operation for the next image.

Figure 6:
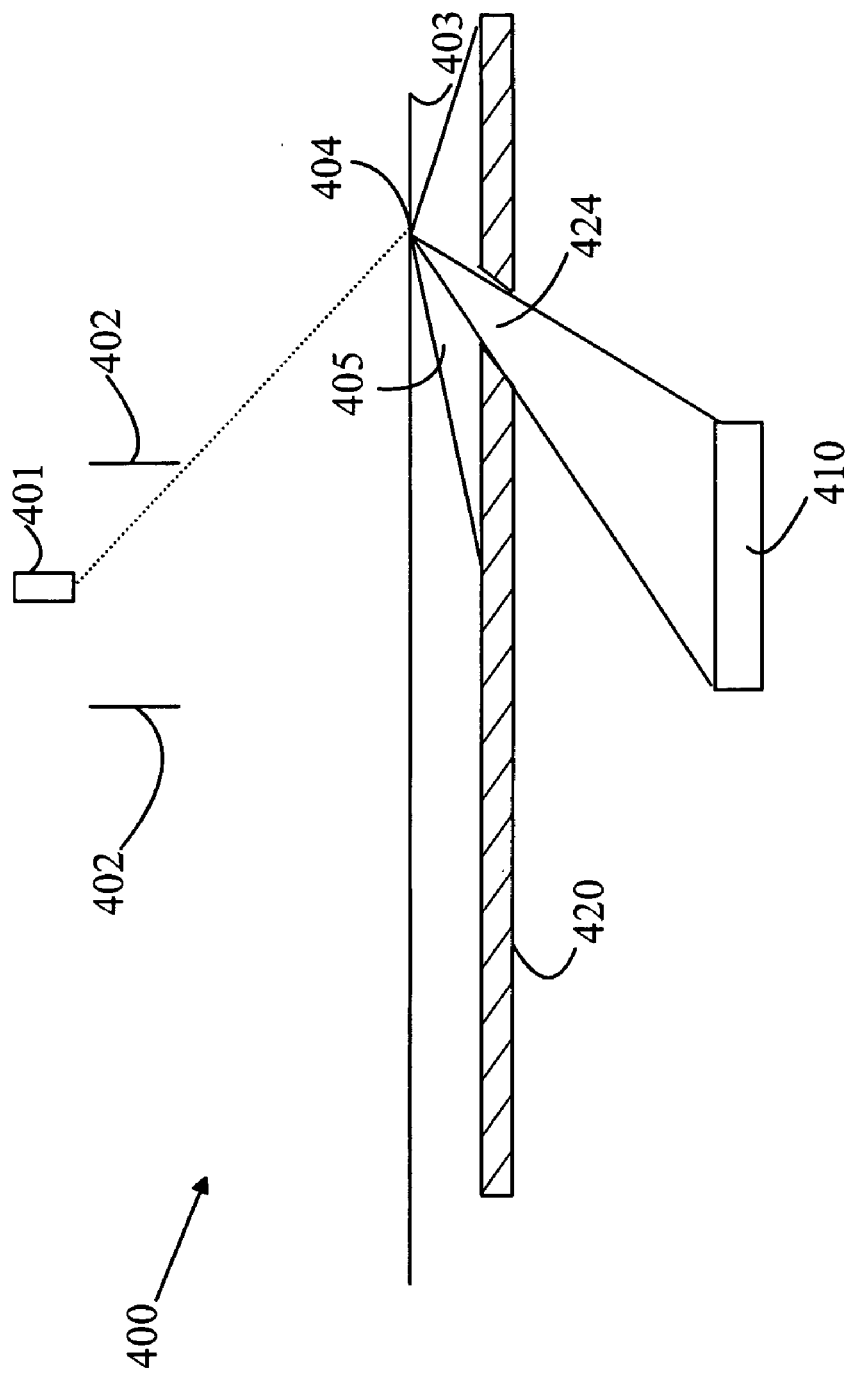
FIG. 6 is a cross-sectional view of an exemplary x-ray source 400 that may be used in other embodiments of the present invention.

The above-described embodiments assume that only the relevant sub-arrays of the detection array receive x-rays at each of the source positions. Refer to FIG. 6, which is a cross-sectional view of an exemplary x-ray source 400 that may be used in these embodiments of the present invention. The X-ray source 400 includes an electron gun 401 and a deflection system 402 that controls the point of impact 404 of the electrons from electron gun 401 on target 403. Target 403 is preferably a two-dimensional sheet of an appropriate metal such as copper. X-rays are emitted at the point of impact of the electrons on target 403 in a broad cone 405. Only a fraction of these x-rays will strike object 410. A collimator constructed from sheet 420 of an x-ray absorptive material that includes a plurality of holes is used to prevent the x-rays that would have missed the object from reaching the detection array. An exemplary collimation hole is shown at 424. In general, the emission positions are fixed; hence, the correct location of each of the holes is known.

The above-described embodiments have been explained in terms of a laminography system. Such systems can be used for generating three-dimensional images by forming images of a number of parallel planes. In addition, the present invention can be used in other imaging configurations in which a number of images that utilize a portion of the detector are to be combined.

Various modifications to the present invention will become apparent to those skilled in the art from the foregoing description and accompanying drawings. Accordingly, the present invention is to be limited solely by the scope of the following claims.

What is claimed is:

1. An imaging system for generating an image of a planar segment of an object, said imaging system comprising:
    an x-ray source that generates x-rays at first and second source points, said x-rays from said first and second source points passing through said object;
    a planar detector comprising a plurality of photodetectors covered by a layer of scintillation material that converts x-rays into visible light, said planar detector being positioned to receive x-rays from said first and second source points after said x-rays have passed through said object; and
    a controller that selects which of said source points generates said x-rays at any given time and that reads a first image formed by x-rays from said first source point and stored in a first portion of said photodetectors while a second portion of said photodetectors measures x-rays from said second source point to generate a second image that is stored in said second portion of said photodetectors.

2. The imaging system of claim 1 wherein said controller combines said first and second images to form an image of a portion of said object.

3. The imaging system of claim 1 wherein said x-ray source further comprises a collimator for preventing x-rays generated at said second source point from reaching said first portion of said photodetectors.

4. The imaging system of claim 1 wherein said x-ray source comprises:
    an electron gun for generating a collimated beam of electrons;
    a target that generates x-rays when bombarded by electrons from said electron gun; and
    a deflection system for positioning said beam of electrons so as to strike said target at selected points thereon,
    wherein said first and second source points correspond to first and second locations on said target.

5. The imaging system of claim 1 wherein said controller resets a third portion of said photodetectors while said second image is being stored in said second portion of said photodetectors.

* * * * *